(12) United States Patent
Kubo (10) Patent No.: US 9,144,368 B2
(45) Date of Patent: Sep. 29, 2015

(54) ENDOSCOPE

(71) Applicant: OLYMPUS CORPORATION, Tokyo (JP)

(72) Inventor: Takafumi Kubo, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/143,439

(22) Filed: Dec. 30, 2013

(65) Prior Publication Data

US 2014/0187864 A1 Jul. 3, 2014

Related U.S. Application Data

(63) Continuation of application No. PCT/JP2013/064640, filed on May 27, 2013.

(30) Foreign Application Priority Data

Sep. 5, 2012 (JP) ................................. 2012-195320

(51) Int. Cl.
*A61B 1/04* (2006.01)
*A61B 1/00* (2006.01)
*G02B 23/24* (2006.01)
(Continued)

(52) U.S. Cl.
CPC .............. *A61B 1/00066* (2013.01); *A61B 1/005* (2013.01); *A61B 1/00114* (2013.01); *A61B 1/015* (2013.01); *A61B 1/07* (2013.01);
(Continued)

(58) Field of Classification Search
CPC ........... A61B 1/00066; A61B 1/00105; A61B 1/012; A61B 1/0011

USPC ................. 600/130, 139, 149, 153, 110, 141; 348/45; 362/574; 396/17
See application file for complete search history.

(56) References Cited

U.S. PATENT DOCUMENTS 6,641,530 B2 * 11/2003 Mitsumori ..................... 600/167
2012/0016191 A1 * 1/2012 Ito et al. ........................ 600/104

FOREIGN PATENT DOCUMENTS

JP 59070908 A 4/1984
JP 64-46001 U 3/1989
(Continued)

OTHER PUBLICATIONS

Japanese Office Action dated Feb. 4, 2014 in related Japanese Patent Application No. 2013-556929.

*Primary Examiner* — Anhtuan T Nguyen
*Assistant Examiner* — Timothy J Neal
(74) *Attorney, Agent, or Firm* — Scully, Scott, Murphy & Presser, PC (57) ABSTRACT

An endoscope includes: an insertion portion; an operation portion provided on a proximal end side of the insertion portion, and including a first and a second sheath bodies; a fluid tube, a light guide fiber bundle, and a signal cable extended from a distal end portion and guided into an internal space of the operation portion; a main board provided in the internal space of the operation portion, wherein the fluid tube, the light guide fiber bundle, and the signal cable are provided on a surface of the main board; and an position regulating member attachable/detachable to/from a predetermined position of the main board, and in a state of being attached to the main board, regulates insertion states of the fluid tubes, the light guide fiber bundle, and the signal cable extended from the insertion portion toward the main board into a predetermined insertion state.

3 Claims, 6 Drawing Sheets (51) Int. Cl.
  *A61B 1/005* (2006.01)
  *A61B 1/015* (2006.01)
  *A61B 1/07* (2006.01)
(52) U.S. Cl.
  CPC ............... *G02B23/24* (2013.01); *A61B 1/0011* (2013.01); *A61B 1/00071* (2013.01)

(56) References Cited

FOREIGN PATENT DOCUMENTS

| | | |
|---|---|---|
| JP | 07-079908 A | 3/1995 |
| JP | 08-036137 A | 2/1996 |
| JP | 09-164111 A | 6/1997 |

* cited by examiner

＃ ENDOSCOPE

CROSS REFERENCE TO RELATED APPLICATION

This application is a continuation application of PCT/JP2013/064640 filed on May 27, 2013 and claims benefit of Japanese Application No. 2012-195320 filed in Japan on Sep. 5, 2012, the entire contents of which are incorporated herein by this reference.

BACKGROUND OF THE INVENTION

1. Field of the Invention

The present invention relates to an endoscope including an operation portion through which internal components of the endoscope such as bending wires, fluid tubes, and a signal cable are inserted.

2. Description of the Related Art

Endoscopes are used in the medical field, the industrial field and other fields. Endoscopes include a so-called electronic endoscope incorporating an image pickup apparatus at a distal end portion of an insertion portion. The medical electronic endoscope (hereinafter "endoscope") 1 shown in FIG. 1 generally includes an operation portion 3 on a proximal end side of an insertion portion 2 which has flexibility.

Figure 1:
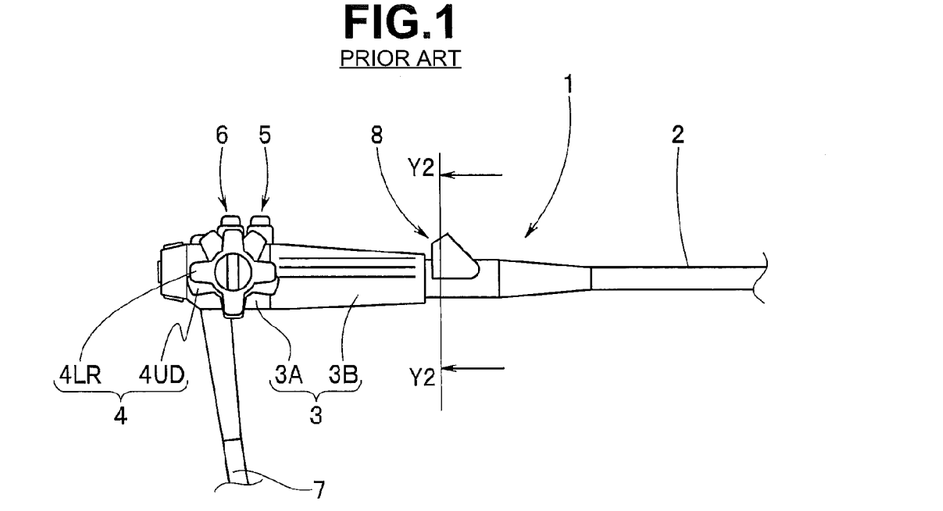
FIG. 1 is a view for illustrating mainly a configuration of an operation portion of an endoscope.

The operation portion 3 is configured by integrally fixing an operation portion main body 3A and a grasping portion case body 3B. The operation portion main body 3A is provided with a bending operation apparatus 4, an air/water feeding button 5, and a suction button 6.

A reference sign 7 represents a universal cable, and the universal cable extends from the operation portion main body 3A.

The bending operation apparatus 4 includes an up/down knob 4UD and a left/right knob 4LR. A bending portion of the insertion portion 2 (not shown) bends in an upper direction or a lower direction in accordance with an operation of the up/down knob 4UD. Also, the bending portion bends in a left direction or a right direction according to an operation of the left/right knob 4LR.

Note that a reference sign 8 represents a treatment instrument insertion port, and the treatment instrument insertion port is provided at a grasping portion case body 3B. The treatment instrument insertion port has an opening through which an endoscope treatment instrument such as forceps, not shown, is inserted and removed.

The endoscope 1 including the bending operation apparatus 4, the air/water feeding button 5 and the suction button 6 includes as the endoscope internal components, the bending wires which extend from the bending portion, and fluid tubes, light guide fiber bundles, a signal cable, and the like, which extend from the distal end portion of the insertion portion (not shown).

Figure 2:
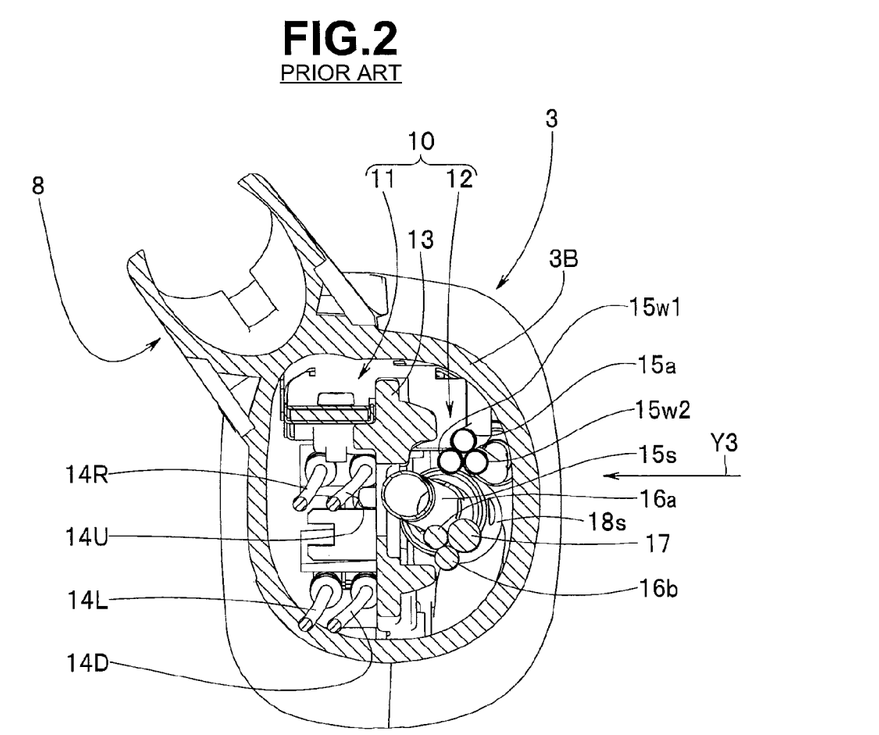
FIG. 2 is a sectional view taken along a line Y2-Y2 of FIG. 1.
Figure 3:
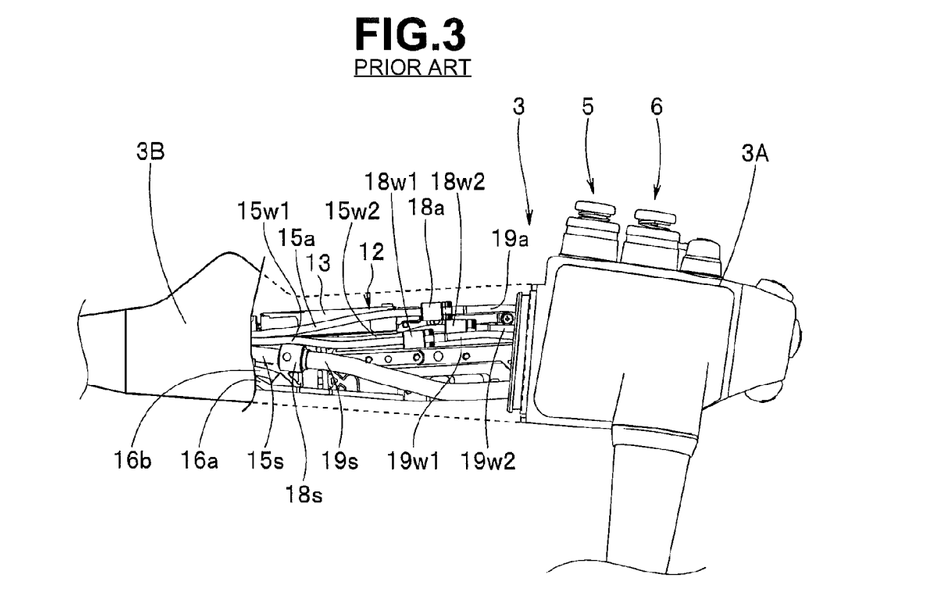
FIG. 3 is a view for illustrating endoscope internal components disposed in a second space which is on one surface side of a main board.

As shown in FIG. 2 and FIG. 3, the endoscope internal components inserted through the insertion portion 2 are passed through the insertion portion 2, and guided into an operation portion internal space 10 that is an internal space of the operation portion 3.

As shown in FIG. 2, the operation portion internal space 10 is divided into two spaces: a first space 11 and a second space 12. A reference sign 13 represents a main board, and the main board divides the operation portion internal space 10. The main board 13 is disposed in parallel with a direction of the longitudinal axis of the operation portion 3.

The bending wires are guided into the first space 11. The bending wires are four bending wires 14U, 14D, 14L and 14R corresponding to four bending directions of the bending portion, i.e., upper, lower, left and right directions.

The fluid tubes, the light guide fiber bundles and the signal cable are guided into the second space 12. The fluid tubes are, for example, an air feeding tube 15a and a water feeding tube 15w1 which correspond to the air/water feeding button 5, and a suction tube 15s and an auxiliary water feeding tube 15w2 which correspond to the suction button 6. For example, the two light guide fiber bundles which are the fiber bundles 16a, 16b (hereinafter "fiber bundles") are provided so as to correspond to the number of illumination windows. The signal cable 17 is extended from the image pickup apparatus (not shown), and configured by a plurality of signal wires combined into one bundle.

As shown in FIG. 3, the air feeding tube 15a, the water feeding tubes 15w1 and 15w2, the suction tube 15s that also serves as a treatment instrument channel tube, the two fiber bundles 16a, 16b, and the signal cable 17 are disposed in the second space 12 constituting one surface side of the main board 13 in the operation portion internal space 10.

One end of the air feeding tube 15a guided into the second space 12 is coupled to one end of a first tube 19a whose other end is coupled to the air/water feeding button 5 via an air feeding tube coupler 18a. One end of the water feeding tube 15w1 guided into the second space 12 is coupled to one end of a second tube 19w1 whose other end is coupled to the air/water feeding button 5 via a first water feeding tube coupler 18w1. One end of the auxiliary water feeding tube 15w2 guided into the second space 12 is coupled to one end of a third tube 19w2 which extends to an endoscope coupler, not shown, via the second water feeding tube coupler 18w2. One end of the suction tube 15s guided into the second space 12 is coupled to one end of a fourth tube 19s whose other end is coupled to the suction button 6 by the suction tube coupler 18s.

The various tubes 15a, 15w1, 15w2, 15s, 19a, 19w1, 19w2 and 19s, the light guide fiber bundles 16a, 16b, and the signal cable 17 each has a predetermined elasticity (or hardness). The various tubes 15a, 15w1, 15w2, 15s, 19a, 19w1, 19w2 and 19s, the light guide fiber bundles 16a, 16b, and the signal cable 17 are disposed to be in a predetermined slack state in the operation portion 3 so as to each reciprocate with respect to a longitudinal direction of the operation portion in the operation portion internal space 10.

Accordingly, the various tube 15a, 15w1, 15w2, 15s, 19a, 19w1, 19w2 and 19s, the light guide fiber bundles 16a, 16b, and the signal cable 17 can be prevented from becoming tight due to a bending action of the bending portion.

Note that the upward bending wire 14U, the downward bending wire 14D, the leftward bending wire 14L, and the rightward bending wire 14R guided into the first space 11 are disposed on the other surface side of the main board 13.

Figure 4:
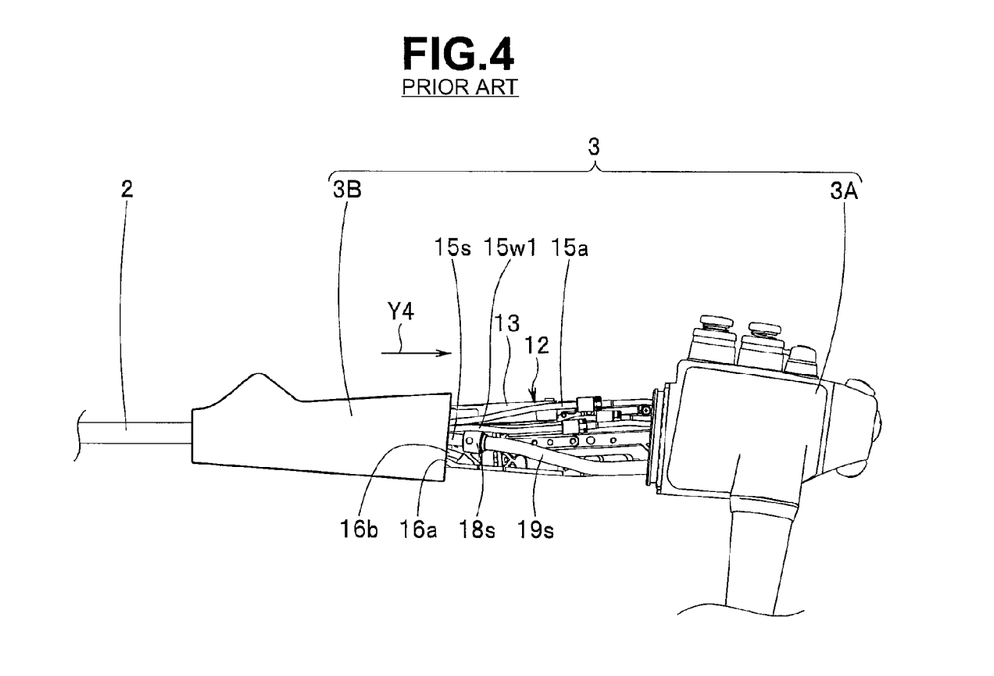
FIG. 4 is a view for illustrating an attachment of a grasping portion case body to an operation portion main body.

After disposing the aforementioned various endoscope internal components, an operator moves the grasping portion case body 3B from the side of the insertion portion 2 to the side of the operation portion main body 3A as shown in an arrow Y4, and integrally combines the operation portion main body 3A and the case body 3B, as shown in FIG. 4.

Japanese Patent Application Laid-Open Publication No. H8-36137 discloses an assembly portion inside the endoscope, which is designed so as to even assembly states of various members, eliminate variation in durability or damages of optical fiber bundles and make the assembling work to be finished in a short time. The assembly portion in the endoscope includes a main board showing an actual layout drawing of various members including optical fiber bundles such as a light guide and an image guide, an air feeding pipe, and a water feeding pipe, which are arranged inside the endoscope operation portion. Assembly sequence numbers are added to marks of the respective members in the layout drawing, and the same numbers are added to the various members to be assembled. As a result, arranging the various members according to the layout drawing and the sequence numbers enables different operators to assemble the various members in the same manner.

An experienced skill is required for a technique of assembling a plurality of endoscope internal components in a short time while keeping a degree of freedom for reciprocation in a longitudinal direction of the operation portion in the internal space of the operation portion.

SUMMARY OF THE INVENTION

An endoscope according to one aspect of the present invention includes: an insertion portion including a distal end portion and a bending portion; an operation portion that is provided on a proximal end side of the insertion portion and includes a first sheath body and a second sheath body, the first sheath body and the second sheath body being attachable to and detachable from each other by moving the second sheath body with respect to the first sheath body in a longitudinal direction of the insertion portion; a fluid tube, a light guide fiber bundle, and a signal cable, which are internal components of the endoscope, extended from the distal end portion, inserted through the insertion portion and guided into an internal space of the operation portion; a main board that is provided in the internal space of the operation portion, wherein the fluid tube, the light guide fiber bundle, and the signal cable are disposed on a surface of the main board; and a position regulating member that has predetermined resilience, is attachable to and detachable from a predetermined position of the main board, and regulates, in a state of being attached to the main board, insertion states of the fluid tube, the light guide fiber bundle, and the signal cable which are extended from the insertion portion toward the main board into a predetermined state.

BRIEF DESCRIPTION OF THE DRAWINGS

FIGS. 5 to 11 are views for one embodiment of the present invention.

DETAILED DESCRIPTION OF THE PREFERRED EMBODIMENT(S)

Hereinafter, an embodiment of the present invention will be described with reference to the drawings.

Since the configuration of the endoscope of the present invention is substantially the same as that of the aforementioned endoscope, the same members are denoted by the same reference signs.

Figure 5:
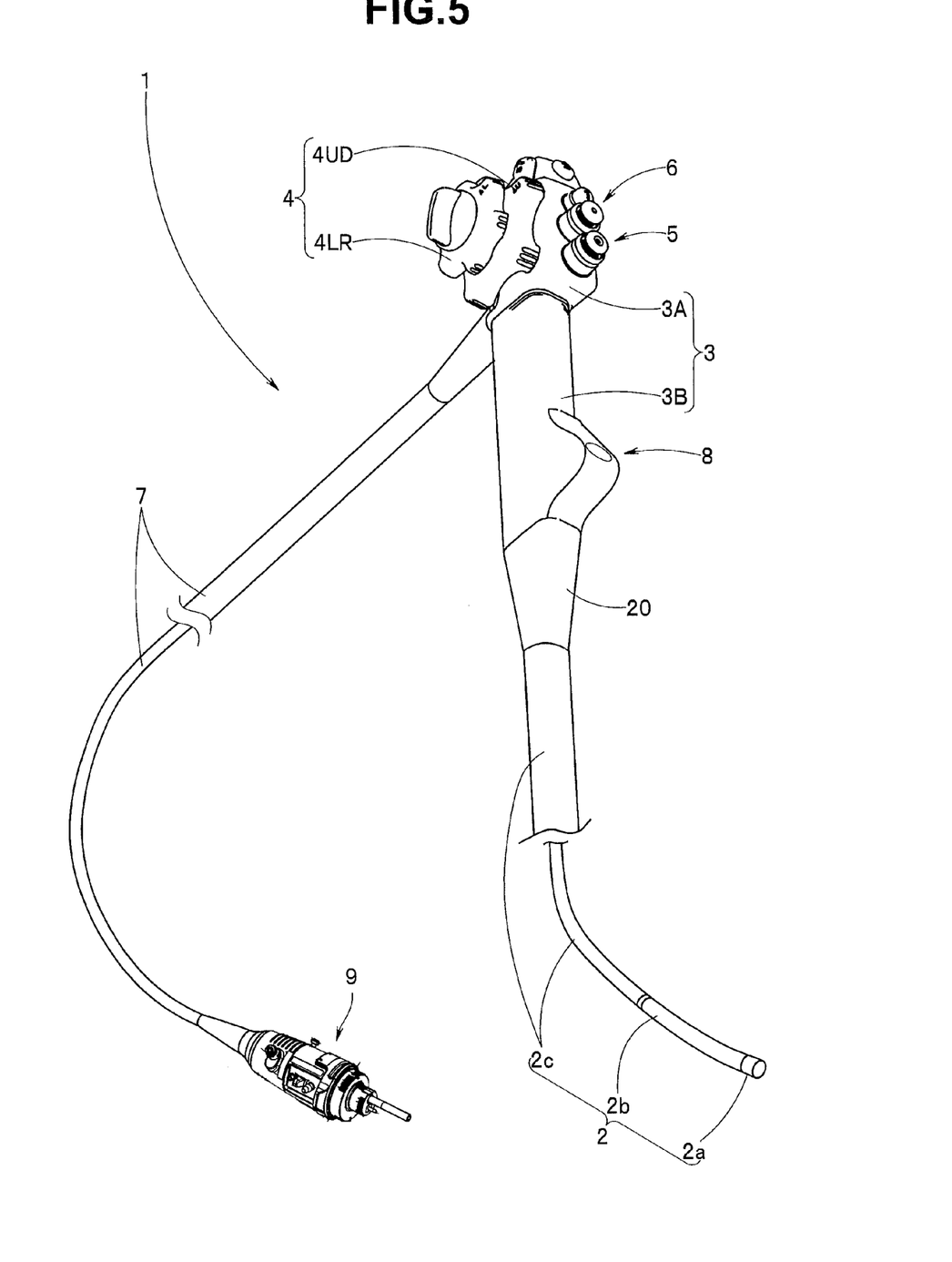
FIG. 5 is a view for illustrating the endoscope.

As shown in FIG. 5, an endoscope 1 in the present embodiment includes an insertion portion 2, an operation portion 3, and a universal cable 7. An endoscope connector 9 is provided at a proximal end portion of the universal cable 7. The endoscope connector 9 is detachably connected to a camera control unit, as an external device, which includes a light source device, for example.

The insertion portion 2 is an elongated member to be inserted into a region to be observed. The insertion portion 2 is configured by connecting in series a distal end portion 2a, a bending portion 2b, and a flexible tube portion 2c. The distal end portion 2a includes an illumination optical system including light guides (see reference signs 16a, 16b of FIG. 8) and an image pickup apparatus including an image pickup device (not shown) such as a CCD and a C-MOS.

For example, one observation window, two illumination windows, one air/water feeding nozzle, one auxiliary water feeding nozzle and one suction opening, which are not shown, are provided on the distal end surface of the distal end portion 2a. The air/water feeding nozzle ejects, for example, air or water toward at least a surface of the observation window. The auxiliary water feeding nozzle is a forward water feeding nozzle and ejects, for example, water toward the observation region whose image is picked up by the image pickup apparatus. The suction opening also serves as a lead-out port for a treatment instrument.

The bending portion 2b is configured to bend in four directions, for example, upper, lower, left and right directions. The flexible tube portion 2c is a tubular member which is long and flexible.

The operation portion 3 is configured by combining an operation portion main body 3A which is a first sheath body and a grasping portion case body 3B which is a second sheath body. The operation portion main body 3A and the grasping portion case body 3B are attachable to and detachable from each other. The operation portion main body 3A is provided with a bending operation apparatus 4, an air/water feeding button 5, a suction button 6, and the like. The bending operation apparatus 4 includes, for example, an up/down knob 4UD and a left/right knob 4LR for bending the bending portion 2b. The grasping portion case body 3B is provided with a treatment instrument insertion port 8, for example. A reference sign 20 represents a bend-preventing member. The bend-preventing member is provided on a distal end side of the grasping portion case body 3B.

The endoscope 1 including the bending operation apparatus 4, the air/water feeding button 5, and the suction button 6 includes, as endoscope internal components, a plurality of bending wires extended from the bending portion 2b, and a plurality of fluid tubes, the two light guide fiber bundles (hereinafter "fiber bundles"), the one signal cable, and the like, which are extended from the distal end portion 2a of the insertion portion 2.

The signal cable is a bundle of a plurality of signal wires. The number of the fiber bundles may be one, or may be three or more.

Figure 6:
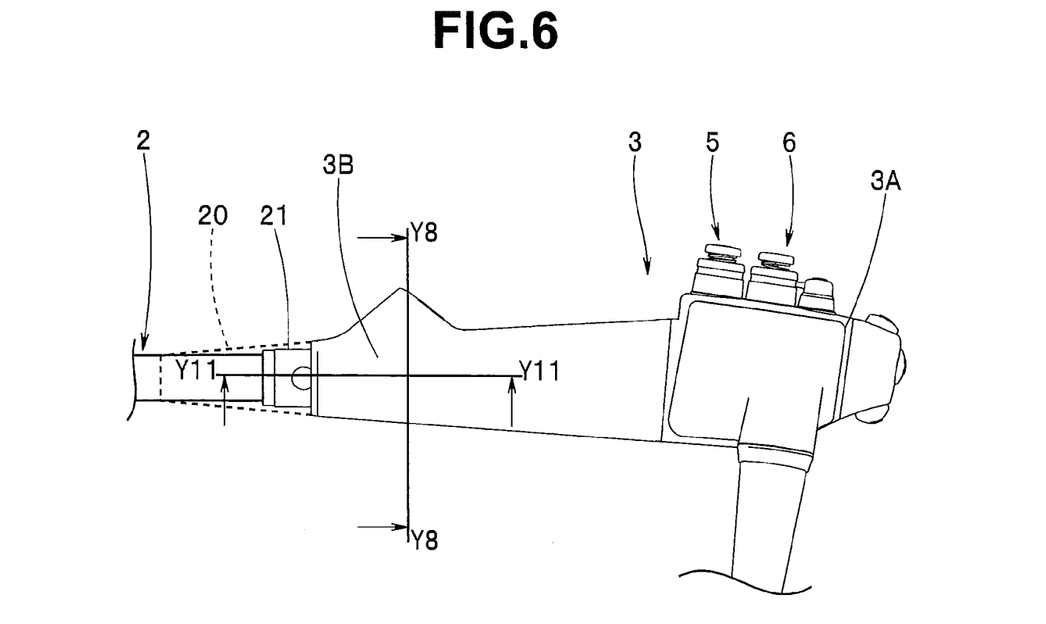
FIG. 6 is a view for illustrating mainly the operation portion of the endoscope of FIG. 5.

As shown in FIG. 6, a proximal end portion of the insertion portion 2 is fixedly coupled to a distal end side of a connection cap 21. A distal end portion of the grasping portion case body 3B is fixedly coupled to the proximal end side of the connection cap 21. The proximal end portion of the insertion portion 2 and the distal end portion of the grasping portion case body 3B are covered with the bend-preventing member 20, and kept in a water-tight manner.

Figure 7:
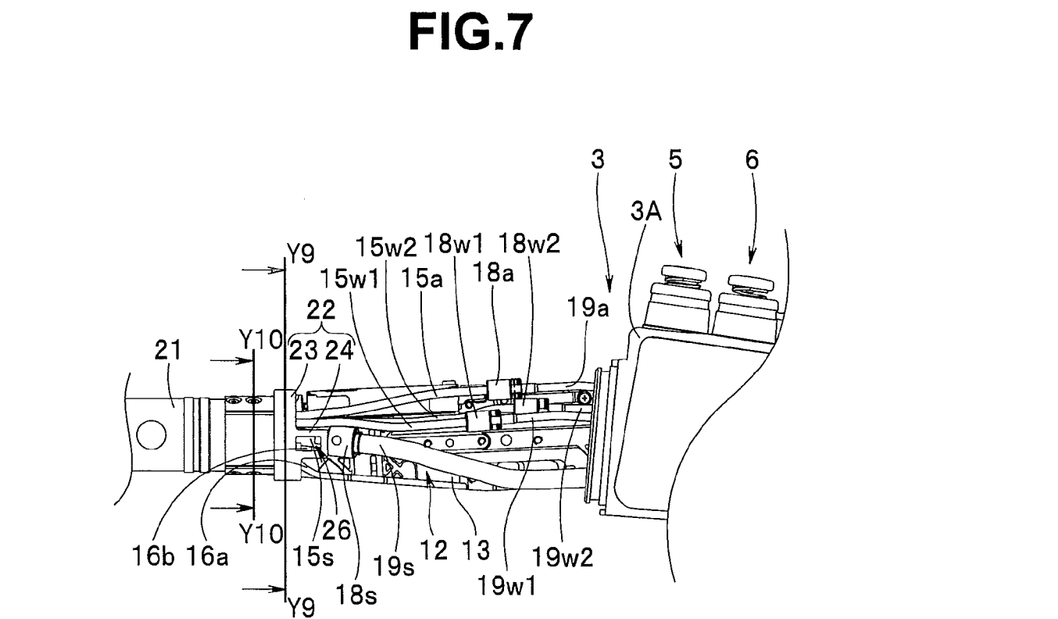
FIG. 7 is a view for illustrating the internal components disposed on a second space side which is on one surface side of the main board.

In the present embodiment, an endoscope internal component position regulating member (hereinafter "regulating member") 22 is provided on the proximal end side of the connection cap 21, namely, the side of the operation portion 3 as shown in FIG. 7.

Figure 8:
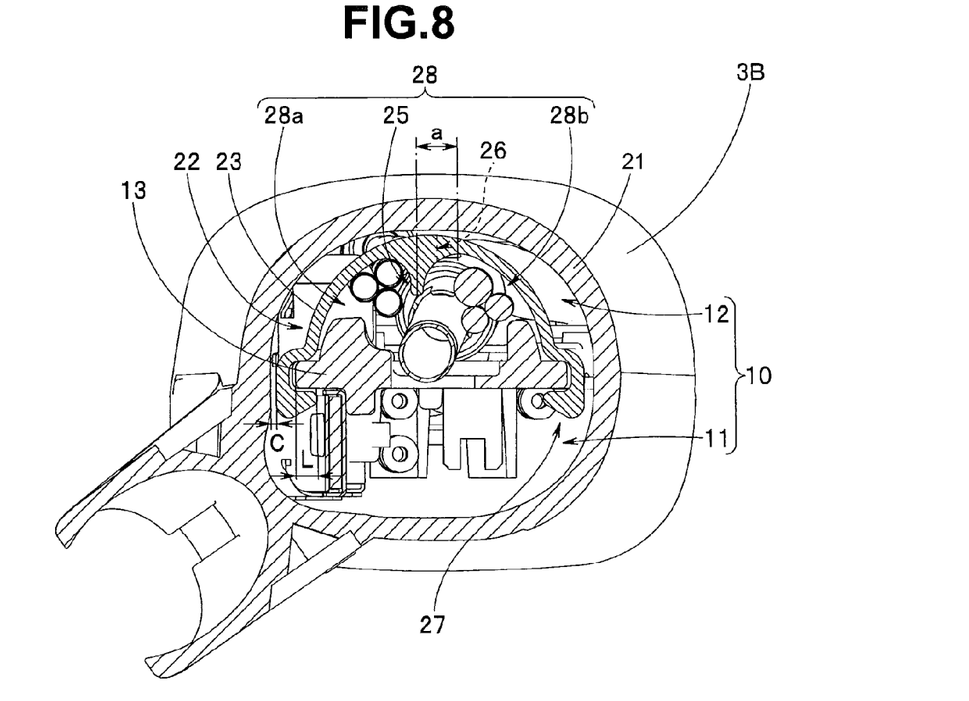
FIG. 8 is a sectional view taken along a line Y8-Y8 of FIG. 6.

As shown in FIG. 8, the regulating member 22 is disposed in an operation portion internal space 10 in the grasping portion case body 3B. Specifically, the regulating member 22 is installed on a one surface side of a main board 13.

The main board 13 is a partitioning member, and partitions the operation portion internal space 10 into a first space 11 and a second space 12. The second space 12 is a space having a substantially semicircular-shaped cross section, and constituted of the one surface of the main board 13 and an inner surface of the grasping portion case body 3B. The first space 11 is a space having a substantially semicircular-shaped cross section, and constituted of the other surface of the main board 13 and the inner surface of the grasping portion case body 3B.

The regulating member 22 is a resin member or a metallic member with a predetermined elasticity that is configured to have an inverted U shape in FIG. 8. The regulating member 22 mainly includes a circular potion 23 shown in FIGS. 7 to 9 and an eaves portion 24 shown in FIG. 7.

The circular potion 23 is a space forming portion and forms a space in which the endoscope internal components are disposed. The eaves portion 24 is a convex piece and protruded from a proximal end surface of the circular potion 23. The eaves portion 24 is set to have a predetermined width dimension and protrude by a predetermined length. The eaves portion 24 prevents a suction tube coupler 18s to be described later and the endoscope internal components from being disposed in an overlapped manner in the second space 12.

A partition portion 25 is provided on the inner surfaces of the circular potion 23 and the eaves portion 24. The partition portion 25 is a convex portion with a predetermined width dimension which is inwardly protruded by a predetermined dimension from the inner surface of the circular potion 23 and the inner surface of the eaves portion 24.

A through hole 26 shown in FIGS. 7 and 8 which communicates the inner and outer surfaces of the eaves is provided at a predetermined position of the eaves portion 24. The through hole 26 has a quadrangular shape, for example. The through hole 26 is an opening for observation to check whether or not the endoscope internal components are overlapped one another during assembly work.

As shown in FIG. 8, in the present embodiment, the center axis of the partition portion 25 is out of alignment with the center line of the through hole 26 by a predetermined dimension a. The partition portion 25 is provided at a thick portion, which is on the left side of the through hole 26 in the drawing.

Figure 9:
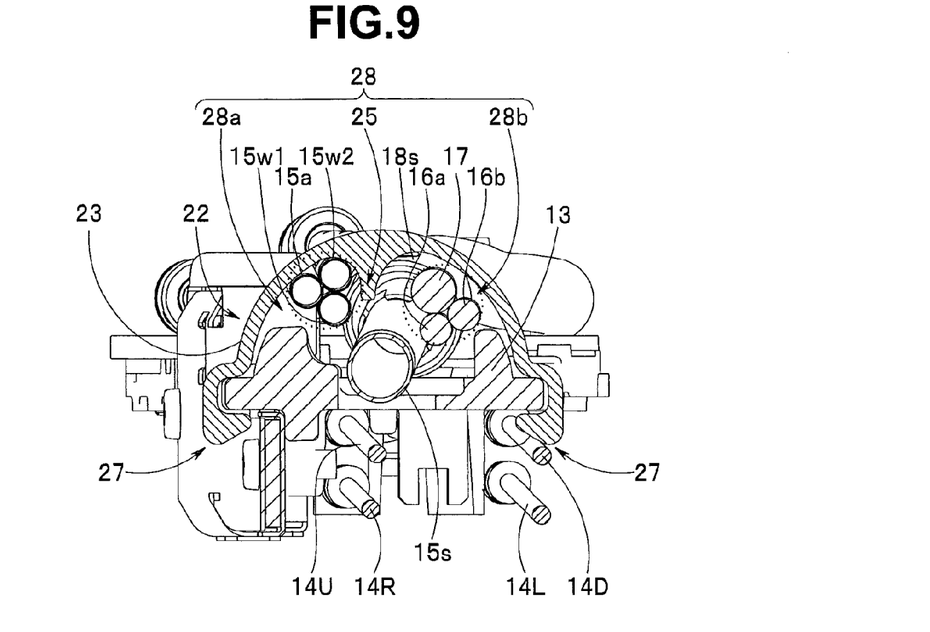
FIG. 9 is a sectional view taken along a line Y9-Y9 of FIG. 7.

As shown in FIG. 9, the circular potion 23 has locking portions 27 at respective end portions. The locking portions 27 are fixedly locked by resilient force at predetermined positions of side portions of the main board 13. The locking portions 27 is locked to the main board 13, thereby constituting an internal component-regulating space 28 formed by the inner surface of the circular potion 23 having the partition portion 25 and the one surface of the main board 13 in the second space 12. The locking portions 27 can be removed from the side portions of the main board 13 by being expanded against the resilient force. That is, the regulating member 22 is attachable to and detachable from the main board 13.

The internal component-regulating space 28 includes a first regulating space 28a and a second regulating space 28b with the partition portion 25 therebetween. In the present embodiment, the first regulating space 28a is configured so as to regulate the degree of freedom of the plurality of fluid tubes in the space 28a to be in a predetermined state, while maintaining the degree of freedom of reciprocation of the tubes in the axis direction. On the other hand, the second regulating space 28b is configured to regulate the degree of freedom of a fluid tube with the biggest diameter, the two fiber bundles and the one signal cable in the space 28b to be in a predetermined state, while maintaining the degree of freedom of reciprocation thereof in the axis direction.

That is, the regulating member 22 is fixedly provided at a predetermined position on a distal end side of the main board 13 dividing the operation portion internal space 10. As a result, as shown in FIG. 8, the internal component-regulating space 28 including the first regulating space 28a and the second regulating space 28b is provided on the distal end side of the second space 12 which is divided by the main board 13.

Figure 10:
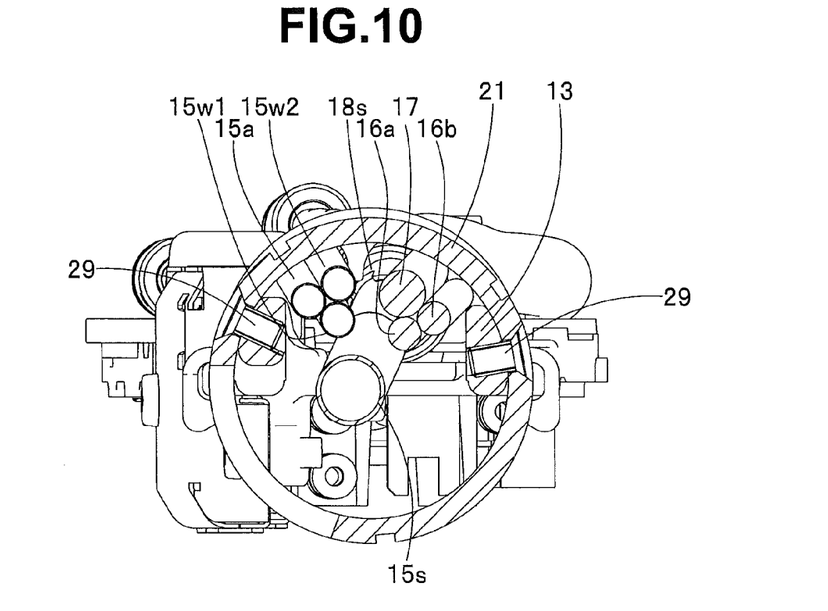
FIG. 10 is a sectional view taken along a line Y10-Y10 of FIG. 7.

With this configuration, the air feeding tube 15a, the water feeding tube 15w1, and the auxiliary water feeding tube 15w2, which are fluid tubes extended from inside the insertion portion 2, are guided into the connection cap 21 shown in FIG. 10, to directly passed through the first regulating space 28a of the internal component-regulating space 28 as shown in FIGS. 8 and 9 without being guided into the second space 12, and then are guided into the second space 12 as shown in FIG. 7.

Consequently, the air feeding tube 15a, the water feeding tube 15w1 and the auxiliary water feeding tube 15w2 guided from the connection cap 21 into the first regulating space 28a are extended to the second space 12 with regulation of degree of freedom in the separating direction, i.e., regulating separation, from the main board 13 while maintaining slackness which enables reciprocation in a direction of a longitudinal axis of the insertion portion in the first regulating space 28a.

On the other hand, the suction tube 15s which has the largest diameter among the fluid tubes extended from inside the insertion portion 2, the first fiber bundle 16a and the second fiber bundle 16b which are the fiber bundles, and the signal cable 17 are guided into the connection cap 21, shown in FIG. 10, to be directly passed through the second regulating space 28b of the internal component-regulating space 28 shown in FIGS. 8 and 9 without being guided into the second space 12, and then guided into the second space 12 as shown in FIG. 7.

As a result, the suction tube 15s, the fiber bundles 16a, 16b, and the signal cable 17 guided into the second regulating space 28b from the connection cap 21 are regulated to be separated from the main board 13 while maintaining slackness which enables reciprocation in the direction of the longitudinal axis of the insertion portion in the second regulating space 28b, and are extended into the second space 12.

Various tubes 15a, 15w1, 15w2, 15s, 19a, 19w1, 19w2, 19s, the fiber bundles 16a, 16b, and the signal cable 17 extended into the second space 12 are disposed in the second space 12.

As shown in FIG. 7, the air feeding tube 15a guided into the second space 12 through the regulating member 22 is coupled to one end of the first tube 19a whose other end is coupled to the air/water feeding button 5 via an air feeding tube coupler 18a. Similarly, the water feeding tube 15w1 guided into the second space 12 is coupled to one end of the second tube 19w1 whose other end is coupled to the air/water feeding button 5 via a first water feeding tube coupler 18w1. Likewise, the auxiliary water feeding tube 15w2 guided into the second space 12 is coupled to one end of a third tube 19w2 via a second water feeding tube coupler 18w2. In a similar manner, the suction tube 15s guided into the second space 12 is coupled to one end of a fourth tube 19s whose other end is coupled to the suction button 6 via the suction tube coupler 18s.

The various tubes 15a, 15w1, 15w2, 15s, 19a, 19w1, 19w2 and 19s, the light guide fiber bundles 16a, 16b, and the signal cable 17 each has a predetermined elasticity (or hardness).

In the present embodiment, the suction tube 15s extended from inside the insertion portion 2 is extended from a lower direction toward an upper direction in FIG. 10, in proximity to the partition portion 25 as shown in FIG. 8, into the second regulating space 28b positioned on the right side of the partition portion 25 shown in FIG. 8, and to the proximal end side of the eaves portion 24 as shown in FIG. 7.

Therefore, the suction tube 15s is brought close to a distal end portion of the partition portion 25 by resilient force of the tube 15s.

As a result, a space for the light guide fiber bundles 16a, 16b, and the signal cable 17 to be inserted through is secured in the second regulating space 28b.

Figure 11:
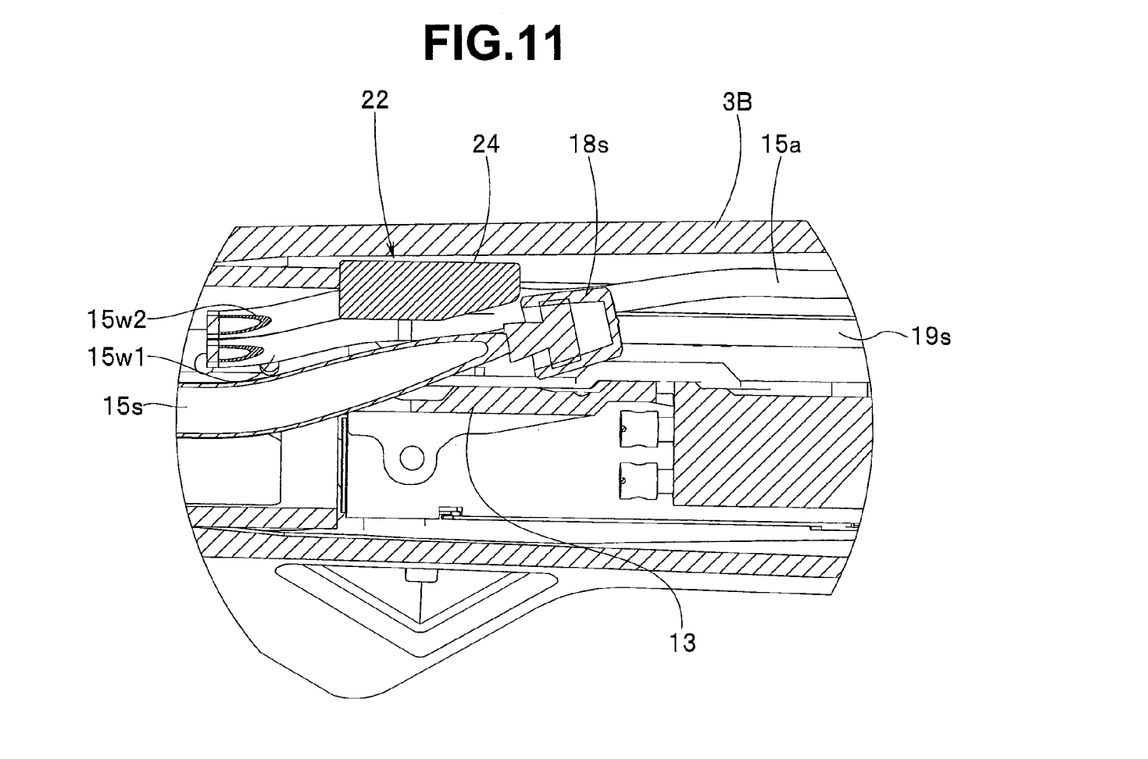
FIG. 11 is a sectional view taken along a line Y11-Y11 of FIG. 6.

As shown in FIG. 11, the maximum outside dimension of a distal end side of the suction tube coupler 18s which couples the suction tube 15s and the fourth tube 19s is set to have substantially the same dimension as the dimension of the gap between a proximal end surface of the eaves portion 24 of the regulating member 22 and the one surface of the main board 13, or a predetermined gap dimension. The gap prevents the suction tube coupler 18s and other endoscope internal components other than the connector 18s from being disposed in an overlapped manner between the inner surface of the eaves portion 24 and the one surface of the main board 13.

Thus, the regulating member 22 including the partition portion 25 is placed on the distal end side of the main board 13, to provide the internal component-regulating space 28 including the first regulating space 28a and the second regulating space 28b on the distal end side in the second space 12, the distal end side being adjacent to the connection cap 21, the second space 12 being divided by the main board 13.

As a result, the plurality of endoscope internal components extended from the connection cap 21 are passed through the regulating spaces 28a and 28b and guided into the second space 12. Thus, the plurality of endoscope internal components are guided into the second space 12 with regulation of degree of freedom in the separating direction from the main board 13 in the regulating spaces 28a, 28b while maintaining the degree of freedom which enables reciprocation in the longitudinal axis direction of the insertion portion in the first regulating space 28a or the second regulating space 28b. Thus, the endoscope internal components can be disposed to have the predetermined slackness while being prevented from being separated from the main board 13 in the second space 12.

It is thus allowed to eliminate the problem that any of the tubes, light guide fiber bundles, and signal cable, which are separated from the main board, contacts the inner surface of the grasping portion case body 3B, and is largely changed in the disposition position, when an operator moves the grasping portion case body 3B from the side of the insertion portion 2 and attaches the grasping portion case body 3B to the operation portion main body 3A.

Providing the through hole 26 at the eaves portion 24 of the regulating member 22 in the eaves portion 24 facilitates visual checking whether or not the suction tube 15s is over-lapped with the fiber bundles 16a, 16b, or the signal cable 17, for example. It is thus allowed to prevent in advance the problem that the endoscope internal components overlap one another inside the regulating member 22.

The center axis of the partition portion 25 provided on the inner surface of the circular potion 23 of the regulating member 22 is out of alignment with the center line of the through hole 26 of the eaves portion 24. This restricts, for example, the disposition position of the suction tube 15s having the largest diameter to be near the partition portion 25 of the second regulating space 28b, which more surely solves the problem that the suction tube 15s overlaps the endoscope internal components in the second regulating space 28b.

In addition, the gap between the inner surface of the eaves portion 24 and the one surface of the main board 13 is restricted to have a predetermined dimension, which prevents the suction tube coupler 18s, and other endoscope internal components except the connector 18s from being disposed in an overlapped manner in the gap. This eliminates problems of degraded functions due to the tubes being pressed, disconnection of wires of the signal cable 17 by being pressed, and breakage of the fibers of the fiber bundles 16a, 16b by being pressed.

In the above-described embodiment, the distal end portion of the main board 13 is integrally fixed at a predetermined position on an inner circumferential surface of the connection member 21 with a screw 29 as shown in FIG. 10. Though not shown in the drawing, the proximal end portion of the main board 13 is integrally fixed at a predetermined position in the operation portion main body 3A constituting the operation portion 3. The main board 13 is disposed along the longitudinal axis of the operation portion 3.

The main board 13 is made of stainless steel, for example, and formed so as to allow various parts provided in the operation portion 3 to be mounted in the optimal state.

The third tube 19w2 is inserted through the operation portion 3 and the universal cable 7, and extended into the endoscope connector 9, and one end of the third tube 19w2 is coupled to an auxiliary water feeding cap (not shown). The light guide fiber bundles 16a, 16b and the signal cable 17 are inserted through the operation portion 3 and the universal cable 7, and extended into the endoscope connector 9, similarly to the third tube 19w2.

As shown in FIG. 9, the bending wires 14U, 14D, 14L, and 14R are guided into the first space 11 and the proximal end portions of the wires are fixed to predetermined positions. This allows the bending wires 14U, 14D to be pulled and relaxed to bend the bending portion 2b in the upper or lower direction, through a rotation operation of the up/down knob 4UD by the operator.

The bending wires 14L, 14R are also allowed to be pulled and relaxed to bend the bending portion 2b in the left direction or the right direction through rotation operation of the left/right knob 4LR by the operator.

In the present embodiment, the locking distance L (see FIG. 8) between each of the locking portions 27 and the main board 13 is set to be longer than a gap C (see FIG. 8) between a side surface of each of the locking portions 27 and the inner surface of the grasping portion case body 3B, which surely prevents the regulating member 22 from coming off in the operation portion internal space 10.

Note that the present invention is not limited to the embodiment described above, and various modifications can be made within the range without departing from the gist of the present invention.

What is claimed is:

1. An endoscope comprising:
an insertion portion comprising a distal end portion and a bending portion;
an operation portion provided on a proximal end side of the insertion portion,
wherein the operation portion comprises a first sheath body and a second sheath body, and
wherein the first sheath body and the second sheath body are attachable to and detachable from each other by moving the second sheath body with respect to the first sheath body in a longitudinal direction of the insertion portion;
a fluid tube, a light guide fiber bundle, and a signal cable, which are internal components of the endoscope, extended from the distal end portion, inserted through the insertion portion and guided into an internal space of the operation portion;
a partitioning member provided in the internal space of the operation portion,
wherein the partitioning member partitions the internal space into a first space and a second space,
wherein the second space is defined by one surface of the partitioning member and an inner surface of the second sheath body, and
wherein the fluid tube, the light guide fiber bundle, and the signal cable are disposed in the second space; and
a position regulating member having a predetermined resilience,
wherein the position regulating member is attachable to and detachable from a predetermined position of the partitioning member,
wherein in a state where the position regulating member is attached to the partitioning member, the position regulating member allows passage of the fluid tube, the light guide fiber bundle, and the signal cable which are extended from the insertion portion, regulates insertion states of the fluid tube, the light guide fiber bundle, and the signal cable into a predetermined state, and guides the fluid tube, the light guide fiber bundle, and the signal cable into the second space, and
wherein the position regulating member comprises:
a space forming portion; and
a pair of locking portions extending from end portions of the space forming portion, respectively, wherein the pair of locking portions are configured to be locked to side portions of the partitioning member,
wherein in a state where the pair of locking portions are locked to the side portions of the partitioning member, an inner surface of the space forming portion defines a regulating space in the internal space to regulate the insertion states of the fluid tube, the light guide fiber bundle, and the signal cable into the predetermined state.

2. The endoscope according to claim 1,
wherein the space forming portion comprises:
a circular portion,
a convex portion protruding inwardly from an inner surface of the circular portion by a predetermined dimension; and
a convex piece having a predetermined width dimension, wherein the convex piece protrudes from a proximal end surface of the circular portion and defines a through hole which communicates an inner surface and an outer surface of the convex piece,
wherein the convex portion is provided to be out of alignment with a center axis of the through hole of the convex piece.

3. The endoscope according to claim 1, wherein a locking distance in a direction orthogonal to the longitudinal direction of the insertion portion where the partitioning member overlaps with each of the pair of locking portions is set to be longer than a gap in the direction orthogonal to the longitudinal direction between a side surface of each of the pair of locking portions and the inner surface of the second sheath body.

* * * * *